United States Patent [19]

Willer et al.

[11] Patent Number: 4,614,800

[45] Date of Patent: Sep. 30, 1986

[54] SYNTHESIS OF CYCLIC DINITRAMINES USEFUL AS EXPLOSIVE AND PROPELLANT INGREDIENTS, GAS GENERANTS AND IN OTHER ORDNANCE APPLICATIONS

[75] Inventors: Rodney L. Willer, New London, Pa.; Ronald L. Atkins, Ridgecrest, Calif.

[73] Assignee: The United States of America as represented by the Secretary of the Navy, Washington, D.C.

[21] Appl. No.: 702,200

[22] Filed: Feb. 15, 1985

[51] Int. Cl.⁴ .......................................... C07D 239/02
[52] U.S. Cl. ................................. 544/335; 544/256; 544/350; 540/475; 548/341
[58] Field of Search ...................... 544/335, 350, 256; 548/341; 260/243.3

[56] References Cited

U.S. PATENT DOCUMENTS 4,443,602  4/1984  Willer ............................... 544/350

OTHER PUBLICATIONS

Harrar et al., J. Electrochem. Soc., vol. 130, No. 1, pp. 108–112, 1983.
Willer et al., J. Org. Chem. 1984, 49, 5147–5154.
Willer et al., Chem. Abst. 102-24604a.

*Primary Examiner*—Donald G. Daus
*Assistant Examiner*—Cecilia Shen
*Attorney, Agent, or Firm*—R. J. Beers; W. Thom Skeer

[57] ABSTRACT

A new one-step synthesis of cyclic 1,3 dinitramines is disclosed. This synthesis utilizes a solution of $N_2O_5$ in 100% nitric acid as the nitrolyzing media. The polynitramines thus produced find utility as explosive and propellant ingredients, gas generants and in other ordnance applications.

6 Claims, No Drawings

SYNTHESIS OF CYCLIC DINITRAMINES USEFUL AS EXPLOSIVE AND PROPELLANT INGREDIENTS, GAS GENERANTS AND IN OTHER ORDNANCE APPLICATIONS

BACKGROUND OF THE INVENTION

1. Field of the Invention

This invention relates to the synthesis of cyclic 1,3 dinitramines. In addition, this invention relates to the preparation of polynitramino compounds that find utility as explosive and propellant ingredients, gas generants and other ordnance applications.

2. Description of the Prior Art

Most synthesis techniques that are currently employed to prepare nitramines involve the cleavage of a protective group from a suitable precursor such as disclosed in U.S. Pat. No. 4,443,602. Such heterolysis reactions often require the use of mixed acid solutions (various mixtures of sulfuric, acetic, acetic anhydride, with nitric acid). One such known technique is the primary nitramine synthesis. This synthesis requires four discrete steps that are time consuming and generally results in low overall yields. Furthermore, it is unsuitable for synthesizing some of the more complicated polynitramines.

SUMMARY OF THE INVENTION

The present invention provides a one-step synthesis which uses a solution of $N_2O_5$ (nitrogen peroxide) in 100% nitric acid as the nitrolyzing media. By this synthesis route, cyclic 1,3 dinitramines as well as more complex nitramines, may be prepared simply, efficiently and in excellent yield.

For example, treatment of trans-1,4,5,8-tetranitoso-1,4,5,8-tetraazadecalin (a bicyclic nitrosamine) with 100% nitric acid yields trans-1,4,5,8-tetraaza-1,4,5,8-trinitro-8-nitrosodecalin in approximately 90% yield. This product must be subjected to nitrolysis in 100% nitric acid a second time to prepare the desired tetranitrodecalin. The overall yield is approximately 50%.

In contrast, treatment of the same trans-1,4,5,8-tetranitroso-1,4,5,8-tetraazadecalin with about 25% to about 30% $N_2O_5$ in 100% nitric acid gives the desired trans-1,4,5,8-tetranitro-1,4,5,8-tetraazadecalin in better than 95% yield in one step.

OBJECTS OF THE INVENTION

It is an object of this invention to provide a means for the preparation of polynitramino compounds.

Another object of this invention resides in the synthesis of cyclic 1,3 dinitramines that may be utilized in a variety of ordnance applications. Yet another object of this invention is a one-step synthesis of new polynitroamino compositions. These and other objects of the invention will become apparent from the following specification and claims.

DETAILED DESCRIPTION OF THE INVENTION

As previously stated, the present invention involves a single step synthesis of polynitramino compounds in which a solution of $N_2O_5$ in 100% nitric acid is utilized as the nitrolyzing media. The $N_2O_5$ solutions are generated by a recently developed electrochemical process (Harrar, J. E.; Pearson, R. K.; *J. Electrochem. Soc., Vol.* 130 No. 1 pp. 108–112, January 1983.

A specified cyclic nitrosamine (cyclic 1,3 dinitrosamine) is reacted with a solution of $N_2O_5$ in 100% nitric acid under controlled reaction conditions. A cyclic 1,3 dinitramine is thus produced in a yield of from about 10 percent to about 95 percent. The lower yields reflect the decomposition of some of the products such as the six-membered compound 1,3-dinitro-1,3-diazacyclohexane, due to decomposition under reaction conditions.

Table I describes the starting materials and yields of the products produced from the reaction of cyclic 1,3-dinitrosamines with solutions of $N_2O_5$ in 100% $HNO_3$.

TABLE I

| PRECURSOR | PRODUCT | PERCENT YIELD |
|---|---|---|
| 1,3-dinitroso-1,3-diazacyclopentane | 1,3-dinitro-1,3-diazacyclopentane | 85% |
| 1,3-dinitroso-1,3-diazacyclohexane | 1,3-dinitro-1,3-diazacyclohexane | 30% |
| 2,4,8,10-tetranitroso-2,4,8,10-tetraazaundencane | 2,4,8,10-tetranitro-2,4,8,10-tetraazaundecane (tetranitraamine) | 94% |
| 4-methyl-1,3-dinitroso-1,3-diazacyclopentane | 4-methyl-1,3-dinitro-1,3-diazacyclopentane | 75% |
| 4-methyl-1,3-dinitroso-1,3-diazacyclohexane | 4-methyl-1,3-dinitro-1,3-diazacyclohexane | >10% |
| Trans-1,4,5,8-tetranitroso-1,4,5,8-tetraazadecalin | Trans-1,4,5,8-tetranitro-1,4,5,8-tetraazadecalin | >95% |

The reason for the relatively low yields of the six-membered compounds 1,3-dinitro-1,3-diazacyclohexane and 4-methyl-1,3-dinitro-1,3-diazacyclohexane is as noted, due to their decomposition under reaction conditions.

The following examples are given to illustrate the invention but should not be considered limiting.

EXAMPLE 1

In a suitable container fitted with a stirrer and cooling bath, 1,3-dinitroso-1,3-diazacyclopentane (10mmole) was slowly added to 10 ml of a well-stirred solution of from about 24 percent to about 30 percent $N_2O_5$ in 100% nitric acid maintained at about minus 30 degrees C. by means of a dry ice dichloroethane slush for about 30 minutes. The cooling bath was then replaced with an ice-water bath, and a stream of dry nitrogen was blown across the surface of the reaction. After about 20 minutes at 0 degrees C., the ice water bath was removed and the solution stirred for about 5 minutes. The contents of the vessel were then poured onto about 50 grams of crushed ice. After the ice had melted, the product was collected by vacuum filtration and washed with water. The yield of 1,3-dinitro-1,3-diazacyclopentane m.p. 132–133 degrees C. was about 85%.

EXAMPLES 2-6

The procedure of Example 1 was followed except that the precursor material was as set forth in Table I. By the disclosed method, 1,3-dinitro-1,3-diazacyclohexane (m.p. 84–86 degrees C., 30% yield), 2,4,8,10-tetranitro-2,4,8,10-tetraazaundecane (m.p. 240–245 degrees C., 94% yield), 4-methyl-1,3-dinitro-1,3-diazacyclopentane (m.p. 79–80 degrees C., 75% yield), 4-methyl-1,3-dinitro-1,3-diazacyclohexane (m.p. 77–78 degrees C., >10% yield) and trans-1,4,5,8-tetranitro-1,4,5,8-tetraazadecalin (m.p. 232–234 degrees C., >95% yield) were synthesized.

While the invention has been described in connection with specific embodiments thereof, it will be understood that it is intended to cover any variation, use or adaptations of the invention. It will, therefore, be recognized that the invention is not to be considered as limited to the precise embodiments shown and described but is to be interpreted as broadly as permitted by the appended claims.

What is claimed is:

1. A method for preparing cyclic 1,3 dinitramines comprising the steps of:

reacting a cyclic 1,3 dinitrosamine with a solution of $N_2O_5$ in 100% nitric acid under controlled reaction conditions; and recovering the cyclic 1,3 dinitramine thus produced.

2. A method according to claim 1 wherein said $N_2O_5$ is present in said solution at from about 25 percent to about 30 percent.

3. A method according to claim 1 wherein said reaction is carried out at about minus 30 degrees C. for about 30 minutes, followed by cooling at about 0 degrees C. for about 20 minutes, product isolation by filtration and water washed.

4. A method according to claim 1 wherein said cyclic 1,3 dinitrosamine is selected from the group consisting of 1,3-dinitroso-1,3-diazacyclopentane; 1,3-dinitroso-1,3-diazacyclohexane; 2,4,8,10-tetranitroso-2,4,8,10-tetraazaundecane; 4-methyl-1,3-dinitroso-1,3-diazacyclopentane; 4-methyl-1,3,-dinitroso-1,3-diazacyclohexane; and trans-1,4,5,8-tetranitroso-1,4,5,8-tetraazadecalin.

5. As a composition of matter, 4-methyl-1,3-dinitro-1,3-diazacyclopentane.

6. As a composition of matter, 4-methyl-1-1,3-dinitro-1,3-diazacyclohexane.

* * * * *